United States Patent [19]

Herd et al.

[11] Patent Number: 4,990,678
[45] Date of Patent: Feb. 5, 1991

[54] PURIFICATION OF HALOGENATED AROMATIC SULFONES OR KETONES

[75] Inventors: Melvin D. Herd, Bartlesville, Okla.; Albert G. Holba, Plano, Tex.; Jimmie J. Straw, Nowata, Okla.

[73] Assignee: Phillips Petroleum Company, Bartlesville, Okla.

[21] Appl. No.: 447,932

[22] Filed: Dec. 8, 1989

[51] Int. Cl.$^5$ .................... C07C 315/06; C07C 49/80
[52] U.S. Cl. ........................................ 568/34; 568/324
[58] Field of Search ................................... 568/34, 324

[56] References Cited

U.S. PATENT DOCUMENTS

| | | | |
|---|---|---|---|
| 3,334,146 | 8/1967 | Pitt et al. | 568/34 |
| 3,726,927 | 4/1973 | Leslie et al. | 568/34 |
| 3,770,832 | 11/1973 | Leslie et al. | 568/34 |
| 4,016,210 | 4/1977 | Horner et al. | 568/34 |
| 4,303,776 | 12/1981 | Baron et al. | 528/171 |
| 4,873,372 | 10/1989 | Schaefer et al. | 568/34 |

FOREIGN PATENT DOCUMENTS

| | | | |
|---|---|---|---|
| 279387 | 8/1988 | European Pat. Off. | 568/34 |
| 2557036 | 6/1977 | Fed. Rep. of Germany | 568/34 |
| 2704972 | 8/1977 | Fed. Rep. of Germany | 568/34 |
| 1308140 | 2/1973 | United Kingdom . | |

*Primary Examiner*—Mary E. Ceperley
*Attorney, Agent, or Firm*—Kenneth D. Goetz

[57] ABSTRACT

A process for purifying a halogenated aromatic sulfone or ketone compound comprising contacting the compound with a solvent having a normal boiling point less than about 225° C. to form a mixture, heating the mixture to a temperature above the normal boiling point of the solvent in a closed system to form a solution, cooling the solution to recrystallize the compound, and recovering the compound. A second embodiment of the invention comprises repeating the purification process steps at least once to further purify the halogenated aromatic sulfone or ketone compound.

21 Claims, No Drawings

PURIFICATION OF HALOGENATED AROMATIC SULFONES OR KETONES

BACKGROUND OF THE INVENTION

This invention relates to a process for purifying halogenated aromatic sulfone or ketone compounds. In a specific aspect, the invention relates to a process for purifying 4,4'-bis(p-chlorophenylsulfonyl)biphenyl.

Halogenated aromatic sulfone or ketone compounds can be produced by the Lewis acid catalyzed condensation of an aromatic hydrocarbon with a halogenated aromatic containing the sulfone or ketone group. For example, 4,4'-bis(p-chlorophenylsulfonyl)biphenyl can be produced by reacting 4-chlorobenzenesulfonyl chloride with biphenyl using nitrobenzene as a solvent in the presence of a Lewis acid catalyst such as ferric chloride or aluminum chloride. The crude 4,4'-bis(p-chlorophenylsulfonyl)biphenyl reaction mixture contains unreacted 4-chlorobenzenesulfonyl chloride, bis(chlorophenyl)sulfone which is an impurity in the 4-chlorobenzenesulfonyl chloride, and 4-(4-chlorophenylsulfonyl)biphenyl which is the mono-halo substituted product.

Purification of applicable halogenated aromatic sulfone or ketone compounds has been a problem due to low solubility in most organic solvents and the very similar or higher solubility of undesirable mono-halo substituted reaction products. For example, when the halogenated aromatic sulfone or ketone compounds are used as monomers for arylene sulfide polymers, these side products must be removed because they act as chain terminators during the polymerization.

Typical recrystallization processes can produce high purity halogenated aromatic sulfone or ketone compounds, but they have the disadvantages of low throughput, difficulty in removing residual solvent, and difficulty in scaling to pilot plant or commercial operations. A purification process which is economical, commercially viable, and can utilize inexpensive solvents to produce high purity product with good yield is highly desirable.

SUMMARY OF THE INVENTION

It is an object of the invention to provide a process for purifying halogenated aromatic sulfone or ketone compounds. It is a further object of the invention to provide an efficient and economic process to purify halogenated aromatic sulfone or ketone compounds that is commericially viable. It is a further object of the invention to provide a process to purify halogenated aromatic sulfone or ketone compounds for use as monomers in the production of high temperature arylene sulfide polymers.

According to the invention, a compound having the structure X-Ar-Y-Ar'-Y-Ar-X, wherein X is a halogen, Y is $-SO_2-$ or $-CO-$, and Ar and Ar' are the same or different and are aromatic radicals of 6 to 14 carbon atoms is purified by contacting the compound with a solvent having a normal boiling point less than about 225° C. to form a mixture, heating the mixture to a temperature above the normal boiling point of the solvent in a closed system to form a solution, cooling the solution to recrystallize the compound, and recovering the compound. In a further embodiment, the purification process steps are repeated at least once to further purify the halogenated aromatic sulfone or ketone compound.

DETAILED DESCRIPTION OF THE INVENTION

Purified halogenated aromatic sulfone or ketone compounds can be used in a variety of applications. For example, the halogenated aromatic sulfone or ketone compounds can be used as monomers in the production of high temperature arylene sulfide polymers. A purification process which enables production of high purity halogenated aromatic sulfone or ketone compounds using relatively inexpensive solvents and relatively short purification time in conventional process equipment is economically preferred.

The process of the invention comprises contacting a compound having the structure X-Ar-Y-Ar'-Y-Ar-X, wherein X is a halogen, Y is $-SO_2-$ or $-CO-$, and Ar and Ar' are the same or different and are aromatic radicals of 6 to 14 carbon atoms with a solvent to form a mixture, heating the mixture to a temperature above the normal boiling point of the solvent in a closed system to form a solution, cooling the solution to recrystallize the compound, and recovering the compound.

The crude halogenated aromatic sulfone or ketone compound can optionally be washed with a solvent prior to purification of the halogenated aromatic sulfone or ketone compound to remove the solvent used during the production of the halogenated aromatic sulfone or ketone compound. Suitable washing solvents are those applicable in the invention.

Applicable halogenated aromatic sulfone or ketone compounds are those which are not very soluble in typical recrystallization solvents at temperatures at or below the normal boiling point of the solvent. Examples of suitable halogenated aromatic sulfones or ketones having the structure X-Ar-Y-Ar'-Y-Ar-X include 4,4'-bis(p-chlorophenylsulfonyl)biphenyl, 4,4'-bis(p-bromophenylsulfonyl)biphenyl, 1,4-bis(p-chlorophenylsulfonyl)benzene, 4,4'-bis(p-chlorobenzoyl)biphenyl, 4,4'-bis(p-bromobenzoyl)biphenyl, 1,4-bis(p-chlorobenzoyl)benzene, 2,6-bis(p-chlorophenylsulfonyl)napthalene, 2,6-bis(p-chlorobenzoyl)naphthalene, and the like. The preferred halogenated aromatic sulfones or ketones are 4,4'-bis(p-chlorophenylsulfonyl)biphenyl and 4,4'-bis(p-chlorobenzoyl)biphenyl.

Applicable solvents for use in the invention are those that have normal boiling points less than about 225° C. The preferred solvents of the invention are those having a normal boiling point less than about 100° C. due to ease of solvent recovery and economics. Suitable solvents are selected from the group consisting of halogenated hydrocarbons, alcohols, ketones, carboxylic acids having no more than 7 carbon atoms, lactams, amides, hydrocarbons, and mixtures thereof. Examples of suitable solvenis include methylene chloride, dichloroethane, chlorobenzene, isopropanol, acetone, methylethylketone, formic acid, acetic acid, butene, benzene, N-methyl-2-pyrrolidone, N,N-dimethylformamide, and mixtures thereof.

In a further embodiment, the applicable solvent comprises solvent recycled from a previous purification plus fresh solvent as make-up. Use of recycled solvent increases the yield of purified halogenated aromatic sulfone or ketone compound.

The weight ratio of solvent to halogenated aromatic sulfone or ketone compound is about 0.5:1 to about 40:1, preferably about 0.75:1 to about 20:1, most preferably about 1:1 to about 10:1. As the weight ratio increases, the temperature required for the purification is reduced.

The temperature used in the process of the invention is above the normal boiling point of the selected solvent, and is from about 80° C. to about 250° C., preferably from about 100° C. to about 220° C., and most preferably from about 120° C. to about 180° C. The temperature selected will be somewhat dependent upon the weight ratio of solvent to halogenated aromatic sulfone or ketone compound selected. In addition, the time the solution is held above the solvents normal boiling point will also depend on the temperature used. However, if the temperature selected is too low, a long hold time will not be sufficient to obtain the desired purity.

The closed system of the invention is preferably a pressure vessel such as a sealed autoclave. The pressure generated during the heating step can be the vapor pressure of the system at the selected temperature or a pressure less than about 500 psig can be applied. If an applied pressure is desired, an inert gas is preferably used to pressurize the system. The inert gas comprises nitrogen, helium, neon and argon. The current preferred inert gas is nitrogen due to its cost and availability.

In a preferred embodiment, after the heating step the mixture of halogenated aromatic sulfone or ketone compound and solvent is held at a temperature above the normal boiling point of the solvent for about 0.15 minute to about 600 minutes, preferably for at least about 1 minute, most preferably for at least about 5 minutes.

In a further embodiment, the purification process comprises repeating the steps of contacting a halogenated aromatic sulfone or ketone compound with a solvent having a normal boiling point less than about 225° C. to form a mixture, heating the mixture to a temperature above the normal boiling point of the solvent in a closed system to form a solution, cooling the solution to recrystallize the compound, and recovering the compound at least once to further purify the halogenated aromatic sulfone or ketone compound. Additional recrystallizations may be necessary depending upon the purity of the starting material, desired product purity, and solvent selected.

The purified halogenated aromatic sulfone or ketone compound can be recovered by any conventional means such as filtration followed by drying.

In a further embodiment, the purified halogenated aromatic sulfone or ketone compound can be washed with a solvent to remove the recrystallization solvent from the purified product during product recovery. Suitable washing solvents are those which are applicable for use in the invention. The preferred solvent for washing is acetone due to its high volatility, economics, and availability.

EXAMPLES

Example I

This example illustrates that purifying a halogenated aromatic sulfone by Soxhlet extraction is a time-consuming process which is neither economical nor commercially viable.

A 481.2 g sample of 4,4'-(bischlorophenyl sulfonyl)-biphenyl (BCPSB), prepared by Friedel-Crafts sulfonylation of biphenyl with 4-chlorobenzenesulfonyl chloride in nitrobenzene was transferred to thimbles for the Soxhlet extractor. Methylene chloride (1600 mL) was charged to a 3 L flask for the extraction process. The Soxhlet extraction was allowed to reflux for 93 hours.

The product was analyzed for its purity by high pressure liquid chromatography (HPLC) with a Waters M-6000A pump using a 4.9 mm by 30 cm Waters porasil column. A Waters model 440 UV detector was used at 254 nm and 2 AUFS for detection along with a Waters 730 data module for recording of chromatograms. Injections were made by a Waters WISP 710A. Flow programming was done by a Waters model 660 solvent programmer.

A typical sample was prepared as follows: Into a 100 ml class A volumetric flask was weighed 0.2 g of sample. Methylene chloride was added to the mark, and the flask was sonicated to promote sample dissolution. A four mL aliquot was filtered through a 0.45 micron filter and placed in the autoinjector. Thirty microliters were injected into the column.

The chromatographic results showed that the purity of BCPSB after Soxhlet extraction was 99.76%.

Example II

This example illustrates a typical pressurized recrystallization process employed in the invention.

Purifications were performed in a one-liter or two-gallon Hastalloy C autoclave manufactured by Autoclave Engineers, Inc. An "anchor" type stirrer was attached to the Magna Drive agitation assembly. In a typical purfication the following were charged to the two-gallon autoclave: 1000 g crude BCPSB (purity 94.5% by HPLC) and 4 kg of methylene chloride, i.e. a solvent to BCPSB weight ratio of 4. The mixture was purged three times with nitrogen, then vented and closed. The mixture was then heated to 140° C. When the temperature reached 140° C., the heating was discontinued and the autoclave allowed to slowly cool. After cooling to room temperature, the purified BCPSB was removed and given 2-3 washes with 200 ml of acetone. The BCPSB was allowed to air dry, and was then analyzed by HPLC as described above. The HPLC results indicated a BCPSB of 99.6% purity was obtained from a crude BCPSB of 94.5% purity. A purity higher than 99.5% is required for use as monomer.

Example III

This example illustrates the effect of the weight ratio of solvent to BCPSB on product recovery and product purity. The purifications were carried out according to the procedure described in Example II except for the differences in weight ratio of solvent to BCPSB, temperature, time and crude BCPSB purity shown with the results in the Table I below.

TABLE I

| Solvent/BCPSB Weight Ratio | Temp. (°C.) | Time (Hr) | Recovery (%) | Crude Purity (%) | Final Product Purity (%) |
|---|---|---|---|---|---|
| 1.00 | 160 | 0.10 | 95.9 | 96.6 | 99.87 |
| 1.79 | 125 | 1.55 | 94.0 | 96.6 | 99.25 |
| 3.98 | 140 | 0.30 | 92.3 | 97.7 | 99.75 |
| 4.51 | 142 | 0.01 | 91.3 | 98.5 | 99.96 |
| 5.30 | 140 | 0.08 | 90.8 | 94.5 | 99.70 |
| 5.57 | 142 | 0.08 | 88.5 | 94.5 | 99.65 |
| 10.00 | 160 | 0.10 | 84.2 | 96.6 | 99.58 |

Although the experiments were not carried out at the same temperature and for the same heating time at the temperatures indicated, the results clearly demonstrate a trend that increasing the solvent to BCPSB weight ratio decreases the product recovery for comparable product purity. The results further demonstrate that excellent product recovery can be obtained without sacrificing the final product purity.

Example IV

This example shows that the length of heating time has little effect on the purification of BCPSB.

The experiment was carried out according to the procedure of Example 11 on a crude BCPSB of 95.5-98.5% purity except that the time held at 140° C. was varied from less than 1 min. to 6 hours. The results are shown in Table II below.

TABLE II

| Time (hours at 140° C.) | Crude BCPSP Purity (%) | Final Product Purity (%) |
| --- | --- | --- |
| 0.008 | 98.5 | 99.96 |
| 0.080 | 97.3 | 99.63 |
| 0.160 | 98.5 | 99.96 |
| 0.300 | 98.4 | 99.50 |
| 1.000 | 97.7 | 99.75 |
| 2.000 | 95.5 | 99.80 |
| 4.000 | 97.7 | 99.70 |
| 6.000 | 96.7 | 99.95 |

The results shown above demonstrate that the invention is so effective that the desired purity is obtained in less than 30 seconds while it requires 93 hours to obtain a similarly satisfactory result by Soxhlet extraction.

Example V

This example illustrates the effect of the final temperature the product is heated to. The experiment was carried out according to the procedure of Example II except that the temperature was heated at 70° C. and held for 3 hours. The purified product was only 97.3% pure. Increasing the temperature to 90° C. with the increase in solvent to BCPSB weight ratio to 10 resulted in a purified product having 99.78% purity. However, the recovery was less than 80%. It was therefore preferable to carry out the inventive process at temperatures higher than 90° C.

Example VI

This example demonstrates that, without pressurization, the purification of BCPSB requires a much longer extraction and recrystallization period to achieve a comparable purity.

To a 2 L one-neck flask, 200.9 g of BCPSB and about 1725 g of methylene chloride (about 8.6 solvent to BCPSB weight ratio) were added. The mixture was refluxed and, at intervals, samples were removed to check the purity. It was found that it took 16.5 hours to reach a purity of 99.6%, a desirable purity for polymerization. However, the recovery was only 80%.

The result suggests that the inventive process (pressurized recrystallization) is a superior process to atmospheric extraction and recrystallization in that it requires a much shorter extraction and recrystallization time, uses less solvent and has a higher product recovery.

Example VII

This experiment was the same as that described in Example II except that the spent solvent from the previous extraction/recrystallization was used for the next extraction/recrystallization. Fresh solvent was added to the recycled solvent to make up the required solvent to BCPSB weight ratio. The results shown in Table III indicate that the use of recycled solvent minimizes the product loss. For instance, the recovery (yield) increased more than 10%, from about 86% to as high as about 99%. It is therefore an economical advantage to use the spent solvent for the invention. It should also be noted that, after 10 recycles, the purity of the product does not decrease sustantially. For example, the purity, as measured by the HPLC method described in Example 11, decreased from 99.9% to 99.56% after 10 recycles.

TABLE III

| Methylene Chloride Recycle[a] | Yield (%) | Purity[b] (Area %) |
| --- | --- | --- |
| 1 | 88.5 | 99.91 |
| 2 | 94.2 | 99.85 |
| 3 | 98.6 | 99.8 |
| 4 | 96.7 | 99.8 |
| 5 | 98.8 | 99.64 |
| 6 | 98.4 | 99.56 |
| 7 | 97.2 | 99.65 |
| 8 | 97.1 | 99.64 |
| 9 | 98.1 | 99.62 |
| 10 | 97.1 | 99.56 |

[a]Methylene chloride is used without purification between recycles; fresh methylene chloride is added to replace handling losses.
[b]Crude purity is 96.85%.

Example VIII

This example further illustrates the invention by employing a higher boiling point solvent and the comparison of the inventive process to an atmospheric extraction employing the same solvent.

To a one-liter stainless steel autoclave, 300 g of BCPSB and mL of dimethylformamide (DMF) was added followed by heating the autoclave, while stirring, and holding at 185° C. for 20 min. Upon being cooled to room temperature, the mixture was removed and filtered, and the product was washed with 500 mL of acetone and air-dried. The recovery was 94.5% and the off white product had a purity of 99.9%. It demonstrates that DMF is an effective solvent for use in the inventive process.

However, similar to using methylene chloride to purify BCPSB at atmospheric pressure (Example VI), non-pressurized purification of BCPSB employing DMF is unsatisfactory. For example, 150 g of BCPSB and 200 mL of DMF were placed in a 3-necked round bottom flask (equipped with condenser and mechanical stirring) and the contents refluxed for an hour. The product was recovered as described above. Analysis showed that the recovery was only 85.7% and the purity was 99.18%.

These results strongly suggest that a pressurized extraction, the inventive process, is far superior to a non-pressurized process.

That which is claimed is:

1. A process for purifying a compound having the structure X-Ar-Y-Ar'-Y-Ar-X, wherein X is a halogen, Y is —$SO_2$— or —CO—, and Ar and Ar' are the same or different and are aromatic radicals of 6 to 14 carbon atoms by pressurized recrystallization comprising:
    (a) contacting said compound with a solvent having a normal boiling point less than about 225° C. to form a mixture wherein said solvent is selected from the group consisting of halogenated hydrocarbons ketones, carboxylic acids having no more than 7 carbon atoms, lactams, amides, hydrocarbons, and mixtures thereof,
    (b) heating said mixture to a temperature above the normal boiling point of said solvent in a closed system having a pressure of at least the vapor pressure of said mixture at said temperature to form a solution, (c) cooling said solution to recrystallize said compound, and (d) recovering said compound.

2. A process according to claim 1 wherein the weight ratio of said solvent to said compound is about 0.5:1 to about 40:1.

3. A process according to claim 2 wherein the weight ratio of said solvent to said compound is about 0.75:1 to about 20:1.

4. A process according to claim 2 wherein said temperature is about 80° C. to about 250° C.

5. A process according to claim 4 wherein said temperature range is about 100° C. to about 220° C.

6. A process according to claim 5 wherein said temperature is about 120° C. to about 180° C.

7. A process according to claim 4 wherein said solvent is a halogenated hydrocarbon.

8. A process according to claim 7 wherein said halogenated hydrocarbon is methylene chlorine.

9. A process according to claim 7 wherein said solvent has a normal boiling point less than about 100° C.

10. A process according to claim 9 wherein said heating is carried out in an inert atmosphere.

11. A process according to claim 10 wherein said compound is 4,4'-bis(p-chlorophenylsulfonyl)biphenyl.

12. A process according to claim 10 wherein said heating is carried out under a pressure less than about 500 psig.

13. A process according to claim 4 wherein said solvent comprises solvent recycled from a previous purification plus fresh solvent as make-up.

14. A process according to claim 12 wherein said mixture is held for about 0.15 minute to about 600 minutes at a temperature above the normal boiling point of said solvent.

15. A process according to claim 14 wherein said mixture is held for at least about one minute at a temperature above the normal boiling point of said solvent.

16. A process according to claim 15 wherein said mixture is held for at least about five minutes at a temperature above the normal boiling point of said solvent.

17. A process according to claim 1 wherein steps (a)–(d) are repeated at least once to further purify said compound.

18. A process according to claim 1 wherein during step (d) said compound is washed with a solvent to remove the recrystallization solvent.

19. A process for purifying 4,4'-bis(p-chlorophenylsulfonyl)biphenyl by pressurized recrystallization comprising:

(a) contacting said 4,4'-bis(p-chlorophenylsulfonyl)biphenyl with a halogenated hydrocarbon to form a mixture, wherein the weight ratio of said halogenated hydrocarbon to said 4,4'-bis(p-chlorophenylsulfonyl)biphenyl is about 0.5:1 to about 40:1, (b) heating said mixture to a temperature of about 80° C. to about 250° C. and holding at said temperature for about 0.15 minute to about 600 minutes in a closed system to form a solution under an inert atmosphere wherein the pressure of said system is from the vapor pressure of said mixture at said temperature to less than about 500 psig, (c) cooling said solution to recrystallize said 4,4'-bis(p-chlorophenylsulfonyl)biphenyl, and (d) recovering said 4,4'-bis(p-chlorophenylsulfonyl)biphenyl.

20. A process according to claim 19 wherein said halogenated hydrocarbon comprises halogenated hydrocarbon recycled from a previous purification plus fresh halogenated hydrocarbon as make-up.

21. A process according to claim 19 wherein said halogenated hydrocarbon is methylene chloride.

* * * * *